US012642712B2

(12) United States Patent
Wirsig et al.

(10) Patent No.: US 12,642,712 B2
(45) Date of Patent: Jun. 2, 2026

(54) REUSABLE SHELL FOR ABSORBENT ARTICLE

(71) Applicant: The Pennington School, Women in STEM Solving Problems ("WISSP"), Pennington, NJ (US)

(72) Inventors: Susan Wirsig, Pennington, NJ (US); Shealyn Tirendi, Pennington, NJ (US); Kira Cafferty, Pennington, NJ (US); Julia McDougall, Pennington, NJ (US); Francesca Pendus, Pennington, NJ (US); Jordan Mahony, Pennington, NJ (US); Elizabeth Adams, Pennington, NJ (US); Ariana Colner, Pennington, NJ (US); Gloria Liu, Pennington, NJ (US); Isabella Fermo, Pennington, NJ (US); Emily Barkley, Pennington, NJ (US); Alexa Lepold, Pennington, NJ (US); Maygala Selvisudhakar, Pennington, NJ (US); Molly Gibbard, Pennington, NJ (US)

(73) Assignee: THE PENNINGTON SCHOOL, Women in STEM Solving Problems ("WISSP"), Pennington, NJ (US)

( * ) Notice: Subject to any disclaimer, the term of this patent is extended or adjusted under 35 U.S.C. 154(b) by 89 days.

(21) Appl. No.: 17/665,816

(22) Filed: Feb. 7, 2022

(65) Prior Publication Data

US 2022/0249301 A1 Aug. 11, 2022

Related U.S. Application Data

(60) Provisional application No. 63/147,464, filed on Feb. 9, 2021.

(51) Int. Cl.
*A61F 13/505* (2006.01)
*A61F 13/15* (2006.01)
(Continued)

(52) U.S. Cl.
CPC ...... *A61F 13/505* (2013.01); *A61F 13/15252* (2013.01); *A61F 13/15756* (2013.01);
(Continued)

(58) Field of Classification Search
CPC .............. A61F 13/505; A61F 13/15252; A61F 13/15756; A61F 13/5616; A61F 13/84; A61F 2013/8497
See application file for complete search history.

(56) References Cited

U.S. PATENT DOCUMENTS

| 1,103,815 | A | * | 7/1914 | Nesgood | ................. A61F 13/64 604/401 |
| 7,137,972 | B1 | * | 11/2006 | Holberg | .............. A61F 13/4915 604/397 |

(Continued)

FOREIGN PATENT DOCUMENTS

| GB | 2508089 | A | * | 5/2014 | ............... A41B 9/04 |

OTHER PUBLICATIONS

Meg Stively, "How to Sew Cloth Pads", Seamwork, May 2020, website: https://www.seamwork.com/craft-projects/how-to-sew-cloth-pads (Year: 2020).*

*Primary Examiner* — Catharine L Anderson
*Assistant Examiner* — Nhu Q. Tran
(74) *Attorney, Agent, or Firm* — Haynes and Boone, LLP

(57) ABSTRACT

The following disclosure presents a wearable reusable shell, configured to hold an absorbent article, for use particularly in economically disadvantaged communities and/or communities with a water shortage. The wearable reusable shell comprises a base having a pair of wings extending from a center portion, an inner layer positioned along the center portion of the base, and an outer layer positioned along the center portion of the base and on top of the inner layer. Extending over the outer layer is at least one band config- (Continued)

ured to hold an disposable absorbent article in place. The present disclosure also presents a hybrid sanitary napkin (and a kit therefor) and methods of making and using a wearable reusable shell.

12 Claims, 6 Drawing Sheets

(51) Int. Cl.
$\quad$ *A61F 13/56* $\qquad$ (2006.01)
$\quad$ *A61F 13/84* $\qquad$ (2006.01)
(52) U.S. Cl.
$\quad$ CPC .......... *A61F 13/5616* (2013.01); *A61F 13/84*
$\qquad$ (2013.01); *A61F 2013/8497* (2013.01)

(56) $\qquad$ References Cited

U.S. PATENT DOCUMENTS

| | | | | |
|---|---|---|---|---|
| 2006/0101558 | A1* | 5/2006 | Coleman | A61F 13/8405 |
| | | | | 2/400 |
| 2015/0157513 | A1* | 6/2015 | Hovey | A61F 13/505 |
| | | | | 604/385.15 |
| 2016/0317361 | A1* | 11/2016 | Mergens | A61F 13/472 |
| 2017/0021051 | A1* | 1/2017 | Richards | A61F 13/53409 |
| 2017/0112683 | A1* | 4/2017 | Fukasawa | A61F 13/4902 |
| 2019/0174839 | A1* | 6/2019 | McGaughy | A41C 3/005 |
| 2019/0389997 | A1* | 12/2019 | Kirchhoefer | C08G 18/4277 |
| 2020/0138647 | A1* | 5/2020 | Jang | A61F 13/622 |
| 2020/0261280 | A1* | 8/2020 | Heyman | A61F 13/471 |
| 2023/0181388 | A1* | 6/2023 | Smith | A61F 13/45 |
| | | | | 604/358 |

* cited by examiner

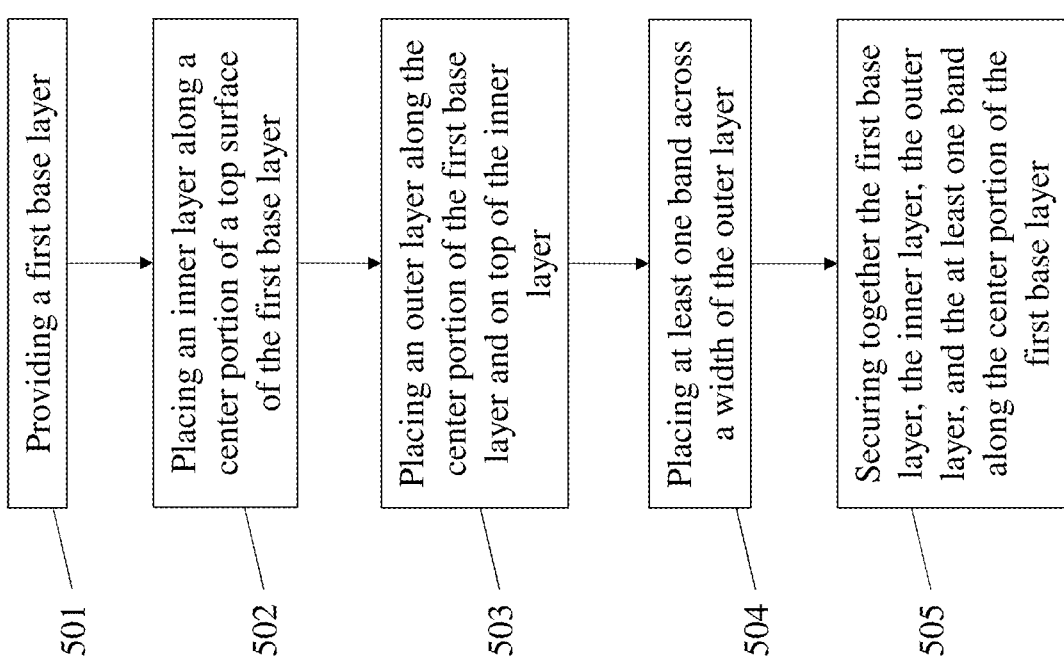

FIG. 5

Providing a first base layer

501

Placing an inner layer along a center portion of a top surface of the first base layer

502

Placing an outer layer along the center portion of the first base layer and on top of the inner layer

503

Placing at least one band across a width of the outer layer

504

Securing together the first base layer, the inner layer, the outer layer, and the at least one band along the center portion of the first base layer

505

500

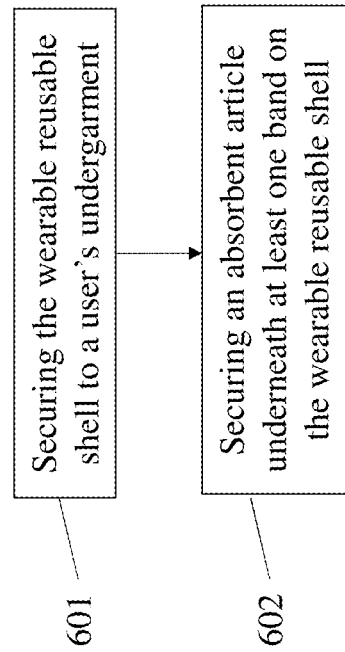
Securing the wearable reusable shell to a user's undergarment
601
Securing an absorbent article underneath at least one band on the wearable reusable shell
602
600
FIG. 6

REUSABLE SHELL FOR ABSORBENT ARTICLE

CROSS REFERENCE TO RELATED APPLICATION

The present application claims priority to U.S. Provisional Application No. 63/147,464 filed on Feb. 9, 2021, the disclosure of which is incorporated herein in its entirety by reference.

FIELD OF THE DISCLOSURE

This disclosure relates to a wearable reusable shell configured to hold a disposable absorbent article for the containment and absorption of bodily excrements.

BACKGROUND

Humanity has always faced a challenge of managing unwanted bodily excrements, such as urine, feces, blood, exudate, and discharge. However, some individuals have the issue of more bodily excrements than others. For instance, some individuals experience natural daily discharge or monthly menses. Others suffer from conditions that cause side effects such as urinary incontinence, bowel incontinence, leaky bladder, loose bowels, diarrhea, irritable bowel syndrome, yeast and bacterial infections, and other chronic ailments that make managing bodily discharge a recurring issue. Finding highly absorbent and effective products to address these conditions is a recurring issue that many of these individuals face. For instance, even current conventional absorbent products (e.g., diapers, panty-liners, menstrual products) occasionally allow for bodily fluids to spill over and leak onto the user's undergarments. It is not uncommon for everyday use and natural movement to allow the absorbent products to become unsecured and move from their position against the user's groin, thus causing the excreted fluid to soil and stain surrounding clothing.

Generally, disposable absorbent products offer a convenient and hygienic solution for managing bodily discharge, as the user may change the product he or she is using as frequently as the user needs. However, some individuals do not have access to, or cannot afford, these disposable products. This can include people living in low-income and low to middle-income communities. Additionally, this can include people living in economically-developing communities and countries. These communities may lack adequate waste management systems or trash disposal, making fully disposable, single-use products cost-prohibitive, wasteful, and unrealistic.

On the opposite end, fully reusable products do not require frequent waste management or disposal. However, they do typically require frequent changing and/or cleaning, which is often messy, unsanitary, and toxic. This is especially an issue when the user must physically touch the liquid/discharge due to poor hygiene or lack of adequate absorbent products. This necessitates frequent trips to the restroom for washing and rinsing. This is not only unsanitary in general, but can be health concern to individuals without access, or with minimal access, to running water.

Menstruation, in particular, presents a unique array of challenges. In some cultures, those who menstruate are disgraced or shamed by the community. When sanitary products are not available, young individuals may stay home while menstruating instead of attending school. In some areas of the world, where penetration before marriage is considered a sin, these individuals are limited to just external sanitary products (e.g., menstrual pads, liners, or sanitary napkins), as opposed to internal sanitary products (tampons, cups, insertable discs, or the like). Because single-use and fully disposable menstrual products are generally cost-prohibitive and wasteful, they are realistically not a feasible option in areas with limited waste management. While fully reusable menstrual pads may offer a more economical and sustainable solution in some communities, this is not often not the case in areas with limited water resources, where young individuals do not have adequate access to clean water to be able to clean their reusable products in a sanitary fashion. In these instances, young individuals are often forced to either place used pads in a bag until they return home to wash them (although carrying a bag to the restroom is an obvious sign of menses, and thus an added source of embarrassment) or to use the same used pad for a prolonged amount of time until they return home (which can cause bacterial infections). This limited access to water may be an issue even at the individual's home, making the process of cleaning the reusable pads at the end of each day a wasteful, and thus discouraged, practice.

A refugee camp, or temporary settlements for people who have been forced to flee their homes because of persecution and/or violence may be one type of community with economic hardship, water shortage, and limited waste management. The combination of limited access to reusable pads and the water shortage (and thus the lack of means for adequate sanitary cleaning) in these communities makes fully reusable pads infeasible for individuals during menses. On the other hand, economic challenges and the limited waste management also makes fully disposable pads undesirable. The lack of adequate menstruation materials makes it particularly challenging for young individuals to attend school while they are menstruating; as such, there is a significant gap between the number of young women and young men or boys who finish secondary education.

In such communities, disposable absorbent articles may be given out as rations. However, the composition of these disposable absorbent articles are generally thin, which allows for bleed through. In addition, these disposable absorbent articles disintegrate quickly, making them difficult to use without anything holding them in place. Finally, there is often a lack of adhesive on the back of these pads, making it difficult for the pads to be held in place.

Thus, there is a need for a wearable reusable shell that can hold a disposable absorbent article in place, thus providing a hybrid, partially reusable and partially disposable, sanitary napkin. Additionally, there is a need for a hybrid sanitary napkin that requires minimal amounts of water for washing and cleaning, while also reducing the amount of disposable waste.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

In one embodiment, the present disclosure provides a wearable reusable shell for an absorbent article wherein the wearable usable shell comprises a base having a pair of wings extending from a center portion, an inner layer positioned along the center portion of the base, and an outer layer positioned along the center portion of the base and on top of the inner layer. Extending over the outer layer is at least one band configured to hold an absorbent article in place. In some embodiments, the absorbent article comprises a disposable material, such as a disposable sanitary pad, toilet paper, or a natural cellulose material. In other embodiments, the absorbent article comprises a reusable material, such as a rag or cloth insert. In other embodiments, the wearable reusable shell may be worn alone, without an absorbent article, such as when the user is experiencing only mild or light menses, or when the user does not have access to absorbent articles.

The base comprises one or more fabric layers. In some embodiments, the one or more fabric layers comprises a fabric printed pattern. For example, a bottom fabric layer may comprise a dark-colored fabric to hide any bleed-through, and a top fabric layer may comprise a printed pattern to provide aesthetic appeal when worn by a user. In some examples, the printed pattern may reflect the culture of the region of use. For instance, a wearable reusable shell made and/or used in a community in Africa may comprise a fabric with a bright and colorful printed pattern that reflects the culture and common stylistic designs of the local African culture. In some embodiments, the fabric comprises a soft material, configured to prevent chafing or irritation when worn against the groin portion and legs of a user.

In some examples, the inner layer comprises a biodegradable material and the outer layer comprises a soft, absorbent material configured to be worn against the groin portion of a user. The outer layer may comprise a dark-colored material in case of any bleed-through or in case the user does not have access to a disposable or reusable absorbent article and is relying solely on the wearable reusable shell for menstrual protection.

In some examples, the at least one band extending over the outer layer is elastic. In some embodiments, an inner surface of the band comprises a rubberized material, such as a silicone strip, to secure an absorbent article in place with a no-slip grip.

In some examples, a mechanical fastener is positioned at an edge portion of each of the pair of wings, wherein the mechanical fastener is configured to secure the wearable reusable shell to an undergarment of a user. In some embodiments, the mechanical fastener comprises at least one of a hook-and-loop fastener, male and female connector, zipper, lip and tape fastener, rivet and eyelet, cufflink, button, snap, clasp, eyelet and lace, and safety pin. In a preferred embodiment, the mechanical fastener is a snap.

In some examples, the wearable reusable shell is may be washed in a washing machine or by hand with soap and water. In some examples, the wearable reusable shell may be reused multiple times or for an extended period of time during a single menstrual cycle, or can be reused across multiple menstrual cycles.

The present disclosure also provides a kit for sanitary napkin comprising the wearable reusable shell described above and an absorbent article configured to be positioned on top of the outer layer and secured underneath the at least one band. In some embodiments, the absorbent article comprises a disposable material, such as a disposable sanitary pad, toilet paper, or a natural cellulose material. In other embodiments, the absorbent article comprises a reusable material, such as a rag or a cloth insert.

The present disclosure further provides a hybrid sanitary napkin comprising a wearable reusable shell, wherein the wearable reusable shell comprises a base having a pair of wings extending from a center portion, a mechanical fastener positioned at an edge portion of each of the pair of wings, wherein the mechanical fastener is configured to secure the wearable reusable shell to an undergarment of a user, an inner layer positioned along the center portion of the base, and an outer layer positioned along the center portion of the base and on top of the inner layer. Extending over the outer layer is at least one band, wherein an inner surface of the at least one band comprises a rubberized material. The hybrid sanitary napkin further comprises an absorbent article positioned on top of the outer layer and secured underneath the at least one band.

The present disclosure further provides a method of making a wearable reusable shell for an absorbent article comprising providing a first base layer, wherein the first base layer comprises a top surface, a bottom surface, and a pair of wings extending from a center portion; placing an inner layer along the center portion of the top surface of the first base layer, wherein the inner layer comprises a biodegradable material; and placing an outer layer along the center portion of the first base layer and on top of the inner layer, wherein the outer layer comprises a soft, absorbent material configured to be worn against the groin portion of a user. At least one band is placed across a width of the outer layer, wherein the at least one band comprises an inner surface comprising a rubberized material. The method further comprises securing together the first base layer, the inner layer, the outer layer, and the at least one band along the center portion of the top surface of the first base layer. In some embodiments, the method further comprises securing a second base layer to the bottom surface of the first base layer.

In some embodiments, the method further comprises securing a mechanical fastener to an edge portion of each of the pair of wings. In some embodiments, the mechanical fastener comprises at least one of a hook-and-loop fastener, male and female connector, zipper, lip and tape fastener, rivet and eyelet, cufflink, button, snap, clasp, eyelet and lace, and safety pin.

The present disclosure further provides a method of using the wearable reusable shell described above, comprising securing the wearable reusable shell to a user's undergarment and securing an absorbent article underneath the at least one band. In some embodiments, the undergarment is underwear, and securing the wearable reusable shell to a user's undergarment comprises fastening together the mechanical fasteners on each of the pair of wings around a groin portion of the underwear. In some embodiments, the absorbent article comprises a disposable material, such as a disposable sanitary pad, toilet paper, or a natural cellulose material. In other embodiments, the absorbent article comprises a reusable material, such as a washable rag or cloth insert. In a preferred embodiment, the absorbent article is disposable.

In yet more detail, the present disclosure is described by the following items which represent preferred embodiments thereof:

1. A wearable reusable shell for an absorbent article comprising:
   a base, wherein the base comprises a pair of wings extending from a center portion;
   an inner layer positioned along the center portion of the base;
   an outer layer positioned along the center portion of the base and on top of the inner layer;

at least one band extending over the outer layer, wherein the at least one band is configured to hold the absorbent article in place; and a mechanical fastener positioned at an edge portion of each of the pair of wings, wherein the mechanical fastener is configured to secure the wearable reusable shell to an undergarment of a user.

2. The wearable reusable shell of Item 1, wherein the inner layer comprises a biodegradable material.

3. The wearable reusable shell of any of the preceding Items, wherein the outer layer comprises a soft, absorbent material, configured to be worn against the groin portion of a user.

4. The wearable reusable shell of any of the preceding Items, wherein the base comprises one or more fabric layers, wherein at least one of the one or more fabric layers comprises a printed pattern.

5. The wearable reusable shell of any of the preceding Items, wherein an inner surface of the at least one band comprises a rubberized material.

6. The wearable reusable shell of any of the preceding Items, wherein the rubberized material is a silicone strip.

7. The wearable reusable shell of any of the preceding Items, wherein the at least one band is elastic.

8. The wearable reusable shell of any of the preceding Items, wherein the mechanical fastener comprises at least one of a hook-and-loop fastener, male and female connector, zipper, lip and tape fastener, rivet and eyelet, cufflink, button, snap, clasp, eyelet and lace, and safety pin.

9. The wearable reusable shell of any of the preceding Items, wherein the mechanical fastener is a snap.

10. A kit for a hybrid sanitary napkin, comprising the wearable reusable shell of Item 1 and an absorbent article configured to be positioned on top of the outer layer and secured underneath the at least one band.

11. A hybrid sanitary napkin comprising:

a wearable reusable shell comprising:

a base, wherein the base comprises a pair of wings extending from a center portion;

an inner layer positioned along the center portion of the base;

an outer layer positioned along the center portion of the base and on top of the inner layer;

at least one band extending over the outer layer, wherein an inner surface of the band comprises a rubberized material; and a mechanical fastener positioned at an edge portion of each of the pair of wings, wherein the mechanical fastener is configured to secure the wearable reusable shell to an undergarment of a user; and an absorbent article positioned on top of the outer layer and secured underneath the at least one band.

12. The hybrid sanitary napkin of Item 11, wherein the absorbent article is reusable.

13. The hybrid sanitary napkin of Item 11, wherein the absorbent article is disposable.

14. A method of making a wearable reusable shell for an absorbent article comprising:

providing a first base layer, wherein the first base layer comprises a top surface, a bottom surface, and a pair of wings extending from a center portion;

placing an inner layer along the center portion of the top surface of the first base layer, wherein the inner layer comprises a biodegradable material;

placing an outer layer along the center portion of the first base layer and on top of the inner layer, wherein the outer layer comprises a soft, absorbent material configured to be worn against the groin portion of a user;

placing at least one band across a width of the outer layer, wherein the at least one band comprises an inner surface comprising a rubberized material; and securing together the first base layer, the inner layer, the outer layer, and the at least one band along the center portion of the first base layer.

15. The method of Item 14, further comprising securing a second base layer to the bottom surface of the first base layer.

16. The method of any of the preceding Items 14-15, further comprising securing a mechanical fastener to an edge portion of each of the pair of wings.

17. The method of any of the preceding Items 15-16, wherein the mechanical fastener comprises at least one of a hook-and-loop fastener, male and female connector, zipper, lip and tape fastener, rivet and eyelet, cufflink, button, snap, clasp, eyelet and lace, and safety pin.

18. A method of using the wearable reusable shell of Item 1, comprising:

securing the wearable reusable shell to a user's undergarment; and securing an absorbent article underneath the at least one band.

19. The method of Item 18, wherein the undergarment is underwear, and wherein securing the wearable reusable shell to a user's undergarment comprises fastening together the mechanical fasteners on each of the pair of wings around a groin portion of the underwear.

20. The method of any of the proceeding Items 18-19, wherein the absorbent article comprises a disposable material.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 5 shows a flowchart detailing an exemplary method of making a wearable reusable shell, according to an embodiment of the present disclosure.

FIG. 6 shows a flowchart detailing an exemplary method of using the wearable reusable shell described herein, according to an embodiment of the present disclosure.

DETAILED DESCRIPTION

Figure 1:
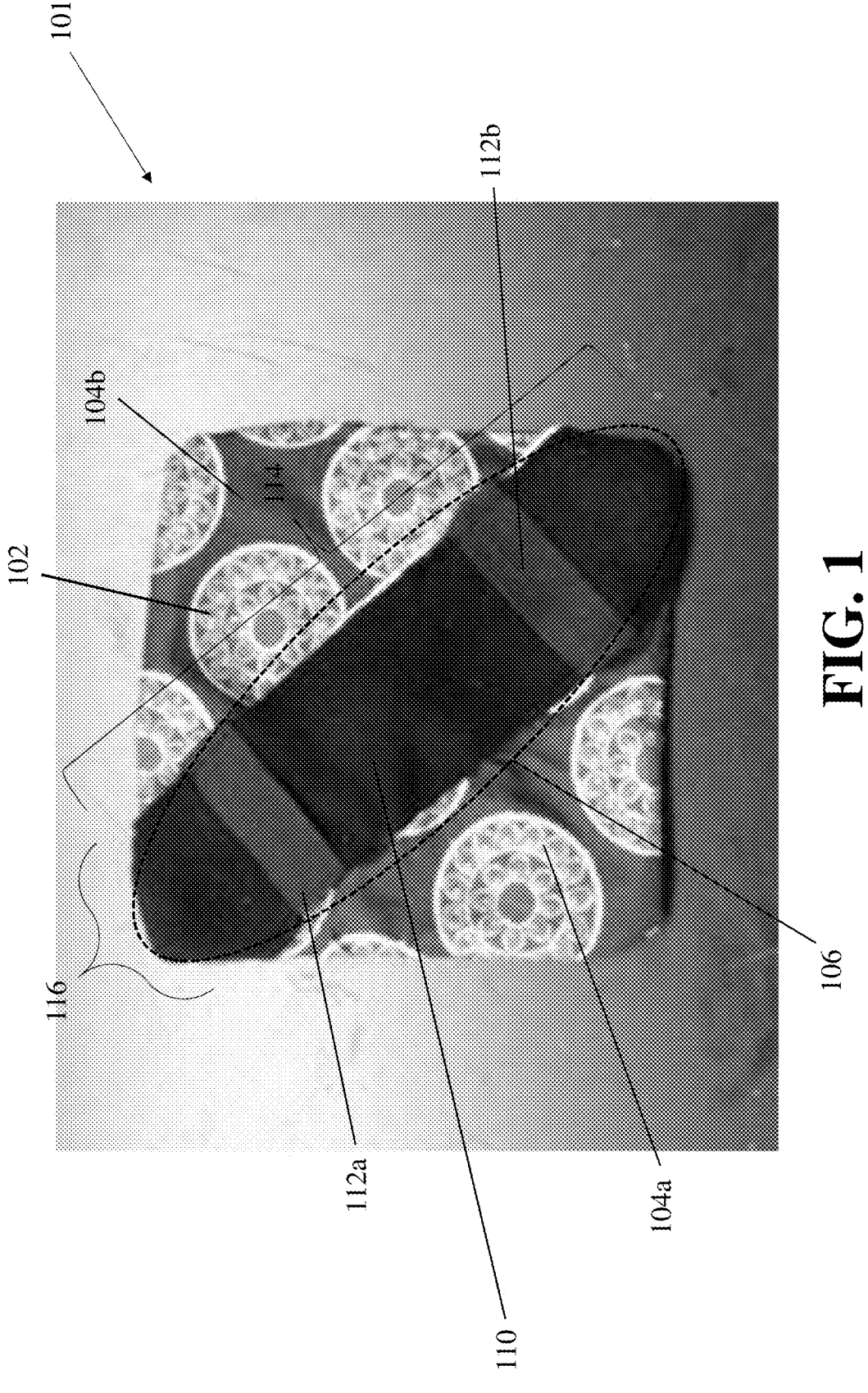
FIG. 1 shows a top view of an exemplary wearable reusable shell, according to an embodiment of the present disclosure.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

To the extent used herein, the term "adjacent" refers to being near or adjoining. Adjacent objects can be spaced apart from one another or can be in actual or direct contact with one another. In some instances, adjacent objects can be coupled to one another or can be formed integrally with one another.

To the extent used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

To the extent used herein, the terms "optional" and "optionally" mean that the subsequently described, component, structure, element, event, circumstance, characteristic, property, etc. may or may not be included or occur and that the description includes instances where the component, structure, element, event, circumstance, characteristic, property, etc. is included or occurs and instances in which it is not or does not.

The present disclosure provides a wearable reusable shell for an absorbent article designed for communities with economic hardship and/or a water shortage. The wearable reusable shell comprises a base, an inner layer comprising a biodegradable material, and an outer layer comprising a soft, absorbent material configured to be worn against the groin portion of a user. The base comprises a pair of wings extending from a center portion, wherein the pair of wings are foldable from an unfolded configuration to a folded configuration. For instance, when the wearable reusable shell is positioned on top of a groin portion of a user's undergarment, the pair of wings may be folded into the folded configuration and wrapped around the groin portion of the undergarment to prevent bodily discharge from leaking onto, and subsequent soiling and staining, the user's clothing. An edge portion of each of the pair of wings comprises a mechanical fastener which may be used to securely fasten the wearable reusable shell to a user's undergarments, such that the wearable reusable shell does not shift upon movement by the user (i.e., the wearable reusable shell stays in place against the groin of a user over the course of everyday movement including walking, sitting, standing up, sleeping, etc.).

The wearable reusable shell may further comprise at least one band extending over the outer layer and configured to hold an absorbent article in place. In some embodiments, an inner surface of the at least one band comprises a rubberized material, such as a silicone strip, to secure the absorbent article in place with a no-slip grip. The wearable reusable shell may be used alone, with the outer layer in direct contact with a user's groin for capturing any bodily fluids or discharge. Using the wearable reusable shell along may be advantageous for when the user is experiencing only mild or light menses, or other bodily discharge, or when the user does not have access to absorbent articles. However, in a preferred embodiment, an absorbent article is positioned on top of the outer layer of the wearable reusable article and secured underneath the at least one band to collect and absorb most of the bodily discharge, before it reaches the wearable reusable shell. The absorbent article may comprise a disposable material, such as a disposable sanitary pad, toilet paper, or a natural cellulose material (e.g., a fibrous vegetable product). In other embodiments, the absorbent article may comprise a reusable material, such as a washable rag or cloth insert. In a preferred embodiment, there is a provided a hybrid sanitary napkin comprising the wearable reusable shell and a disposable absorbent article positioned on the outer layer and secured underneath the at least one band. This hybrid—partially reusable and partially disposable—sanitary napkin creates a reduced amount of disposable waste (compared to fully disposable menstrual products) and the wearable reusable shell, collecting only that bodily discharge that seeps through the disposable absorbent article, requires a reduced amount of water for washing and cleaning (compared to fully reusable menstrual products).

Thus, the wearable reusable shell and the hybrid sanitary napkin create a unique solution for managing menses for individuals residing in areas of the world with economic hardship, water shortage, and limited waste management (e.g., a refugee camp). Ultimately, the wearable reusable shell and hybrid sanitary napkin may be used to increase school attendance young individuals and reduce social taboos surrounding menstruation and ostracism of half of the community population.

FIG. 1 shows a top view of an exemplary wearable reusable shell 101 for an absorbent article, according to an embodiment of the present disclosure. The wearable reusable shell 101 comprises a base 102, wherein the base 102 comprises a pair of wings 104a, 104b extending from a center portion 106. An inner layer 108 (shown in FIG. 3) is positioned along the center portion 106 of the base 102. An outer layer 110 is positioned along the center portion 106 and on top of the inner layer 108. At least one band 112a, 112b extends over the outer layer 110, wherein the at least one band 112a, 112b is configured to hold an absorbent article (not shown).

The base 102 may comprise one or more layers (see 102a, 102b in FIG. 3) comprising a fabric material. Exemplary fabric materials include, but are not limited to the following: cotton, polyester, wool, yarn, chiffon, fleece, felt, synthetic fabrics, natural cellulose materials, and blends thereof. In some embodiments, the one or more base layers 102a, 102b comprises a fabric printed pattern. For example, a first base layer 102a may comprise a top fabric layer comprising a printed pattern to provide aesthetic appeal when worn by a user, wherein a second base layer 102a may comprise a dark-colored fabric to hide any bleed-through of discharge that seeps through the first base layer 102a. In other embodiments, both the first and second base layers 102a, 102b may comprise a printed pattern. In some examples, the printed pattern may reflect the culture of the region of use. For instance, a base 102 for a wearable reusable shell 101 may comprise a fabric with a printed pattern which reflects the bright, vibrant colors of the local African culture. In some embodiments, the fabric comprises a soft material, configured to prevent chafing or irritation when worn against the groin portion and inner thighs of a user.

As shown in FIG. 1, the base 102 comprises a square shape or diamond shape, but the shape of the base 102 is not limited for purposes of this disclosure. The base 102 comprises a pair of wings 104a, 104b extending from a center portion 106. The center portion 106 has a longer length 114 than width 116. For example, the length 114 and the width 116 of the center portion 106 are configured to be approximately the size of a groin portion of a user's underwear. In some examples, the length 114 and the width 116 of the center portion 106 vary according to a preference and/or size of the user. The pair of wings 104a, 104b are foldable from an unfolded configuration (see, e.g., FIG. 1) to a folded configuration (see, e.g., FIG. 4). For instance, when the wearable reusable shell 101 is positioned on top of a groin portion of a user's undergarment, the pair of wings 104a, 104b may be folded into the folded configuration and wrapped around the groin portion of the undergarment (not shown) to prevent bodily discharge from leaking onto, and subsequent soiling and staining, the user's clothing. In a non-limiting example, the undergarment may be underwear, briefs, thongs, boxers, spandex, spanx, or other body shaper.

Figure 2:
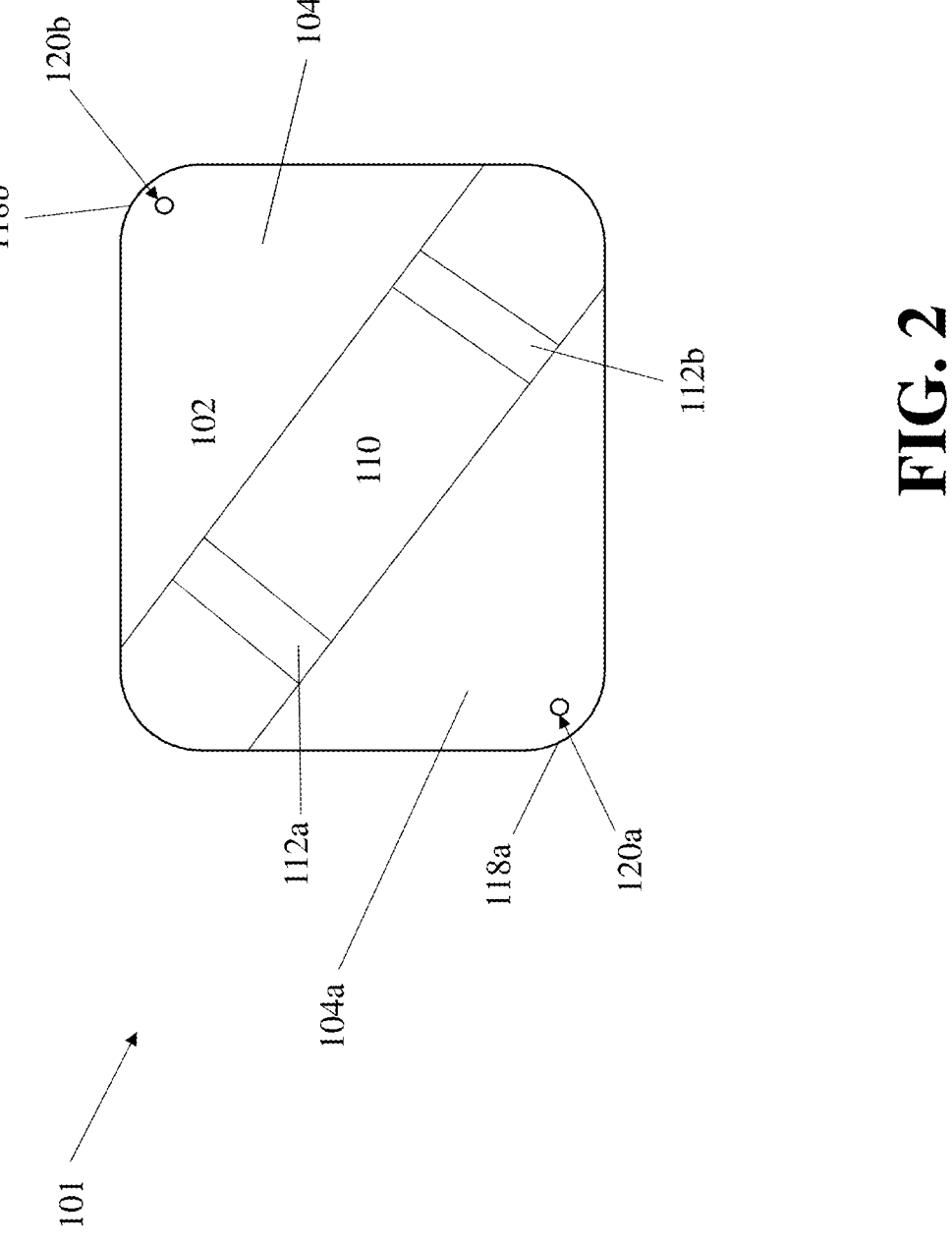
FIG. 2 shows a schematic top view of an exemplary wearable reusable shell, according to an embodiment of the present disclosure.

In some embodiments, as shown in FIG. 2, an edge portion 118a, 118b of each of the pair of wings 104a, 104b of the base 102 comprises a mechanical fastener 120a, 120b which may be used to securely fasten the wearable reusable shell 101 to a user's undergarment. Mechanical fasteners 120a, 120b are configured to couple to each other. Accordingly, in some configurations, the mechanical fasteners 120a, 120b secure the wearable reusable shell 101 around the groin portion of a user's undergarment, such that the wearable reusable shell 101 does not shift upon movement by the user (i.e., the wearable reusable shell stays in place against the groin of a user over the course of everyday movement including walking, sitting, standing up, sleeping, etc.). Mechanical fasteners 120a, 120b may comprise, for instance, at least one of hook-and-loop fasteners, male and female connectors, zippers, lip and tape fasteners, rivets and eyelets, cufflinks, buttons, snaps, clasps, eyelets and lace, and safety pins. In some embodiments, such as where the base 102 comprises a plurality of layers (102a, 102b), the mechanical fasteners 120a, 120b may extend through or protrude through each base layer 102a, 102b.

Figure 3:
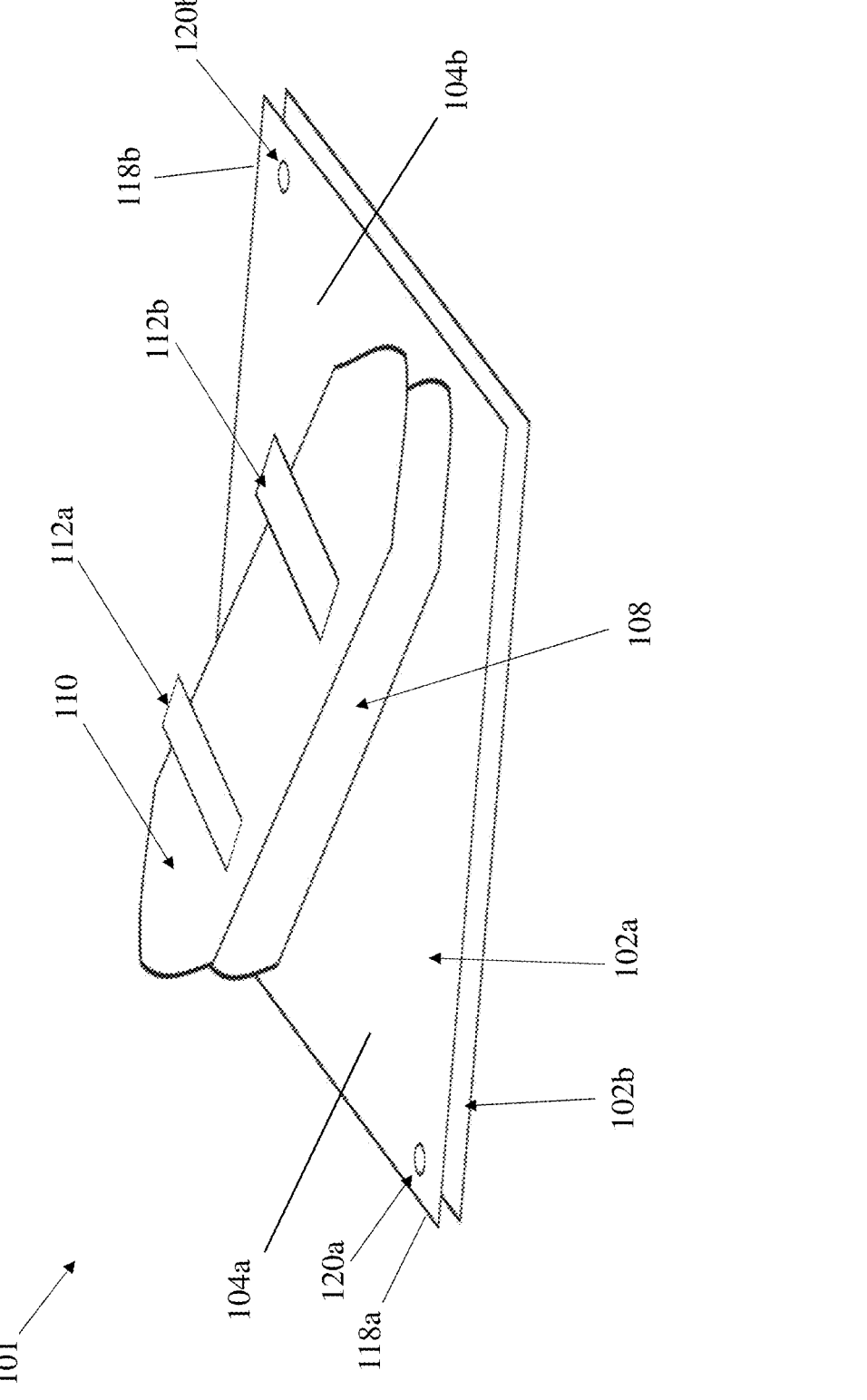
FIG. 3 shows an exploded planar view of an exemplary wearable reusable shell, according to an embodiment of the present disclosure.

FIG. 3 shows an exploded planar view of an exemplary wearable reusable shell 101, according to an embodiment of the present disclosure. Outer layer 110 and inner layer 108 may be sized to align with the size and dimensions of the center portion 106 of the base 102. In some embodiments, the outer layer 110 and inner layer 108 may have the same dimensions, such that when the outer layer 110 is placed along the center portion 106 and on top of the inner layer 108, the inner layer 108 may not be visible from a top view of the wearable reusable shell 101 (see, e.g., FIGS. 1-2). The outer layer 110 and inner layer 108 may comprise a rectangular, oval, oblong, or missile shape, although the shape is not particularly limited for purposes of the present disclosure.

Outer layer 110 may comprise a material that is sufficiently thick and absorbent so as to absorb bodily fluids or discharge (including heavy menses) and minimize leakage through to the inner layer 108 and onto a user's clothing. In some embodiments, such as when the wearable reusable shell 101 is worn alone without an absorbent article, the outer layer 110 is be configured to be worn directly against the groin portion of a user. As such, outer layer 110 may further comprise a soft and comfortable (e.g., not scratchy, itchy, or abrasive) material. Exemplary soft, absorbent materials that may be used for the outer layer 110 include, but are not limited to: cotton, polyester, wool, yarn, chiffon, fleece, felt, synthetic fabrics, natural cellulose materials, and blends thereof. In a preferred embodiment, outer layer 110 comprises fleece. In a further preferred embodiment, the outer layer 110 comprises a dark-colored material to hide or disguise color of some natural bodily fluids or discharge (e.g., blood or feces).

Inner layer 108 may comprise an absorbent material for capturing any bodily fluids that may seep through the outer layer 110 and preventing further leakage of bodily fluids and discharge onto a user's clothing. In some embodiments, the inner layer 108 comprises a biodegradable and/or absorbent material. Exemplary biodegradable and/or absorbent materials include, but are not limited to: cotton, polyester, wool, yarn, chiffon, fleece, felt, synthetic fabrics, natural cellulose materials (e.g., bamboo), and blends thereof. In a preferred embodiment, the inner layer 108 comprises cotton batting. In some embodiments, outer layer 110 and inner layer 108 may comprise the same material. In other embodiments, the outer layer 110 may comprise a different material than inner layer 108.

The wearable reusable shell 101 further comprises at least one band 112a, 112b that extends over the width of the outer layer 110 and is configured to hold an absorbent article (not shown) in place on the wearable reusable shell 101. In some embodiments, the at least one band 112a, 112b is elastic or flexible, such that an absorbent article may be fitted and secured underneath the at least one band 112a, 112b along a top surface of the outer layer 110. In some embodiments, an inner surface of the at least one band 112*a*, 112*b* may comprise a rubberized material, such as a silicone strip, to ensure a no-slip grip on the absorbent article. The at least one band 112*a*, 112*b* may comprise a plurality of bands and the number of bands is not particularly limited. In a preferred embodiment, the at least one band 112*a*, 112*b* comprises two bands, as shown in FIGS. 1-3. The at least one band 112*a*, 112*b* may be positioned anywhere along a length of the outer layer 110. In a preferred embodiment, the bands 112*a*, 112*b* are positioned at distal ends of the outer layer 110, so as to not rub directly against a groin portion of a user, which may cause discomfort, and to minimize interference with the capturing of bodily fluids by the absorbent article secured thereunder. The type of material of the bands 112*a*, 112*b* is not limited for purposes of the present disclosure, and may include at least one of cotton, polyester, spandex, nylon, and terry cloth. In a preferred embodiment, the bands 112*a*, 112*b* comprise a washable material. The base 102, inner layer 108, outer layer 110, and the at least one band 112*a*, 112*b* may be secured together, for instance via sewing or stitching, so as to create one integrative wearable reusable shell 101.

In some embodiments, the absorbent article (not shown) secured underneath the at least one band 112*a*, 112*b* comprises a disposable material, such as a disposable sanitary pad (e.g., a pantiliner), toilet paper, or a natural cellulose material (e.g., a fibrous vegetable product). In other embodiments, the absorbent article comprises a reusable material, such as a washable rag or a cloth or fabric insert. In a preferred embodiment, the absorbent article is disposable, such that the disposable absorbent article together with the wearable reusable shell 101 as described herein forms a hybrid sanitary napkin. This hybrid, partially reusable and partially disposable, sanitary napkin creates a reduced amount of disposable waste (compared to fully disposable menstrual products) and the wearable reusable shell 101, collecting only that bodily discharge that seeps through the disposable absorbent article, requires a reduced amount of water for washing and cleaning (compared to fully reusable menstrual products).

Upon use of the hybrid sanitary napkin, most of the bodily fluids or discharge will be captured and absorbed by the disposable absorbent article. Any additional overflow or leakage will be captured by the wearable reusable shell 101. Once the used absorbent article is removed from underneath the at least one band 112*a*, 112*b*, separated from the wearable reusable shell 101 and disposed of, the wearable reusable shell 101 may be washed with soap and water and hung or laid out to dry. Preferably, the wearable reusable shell 101 is washed at least once per menstrual cycle, or whenever spillage or leakage of bodily fluids or discharge is spotted on the wearable reusable shell 101. The wearable reusable shell 101 is configured to be washed and dried multiple times so as to prevent infection and inhibit bacterial growth.

Figure 4:
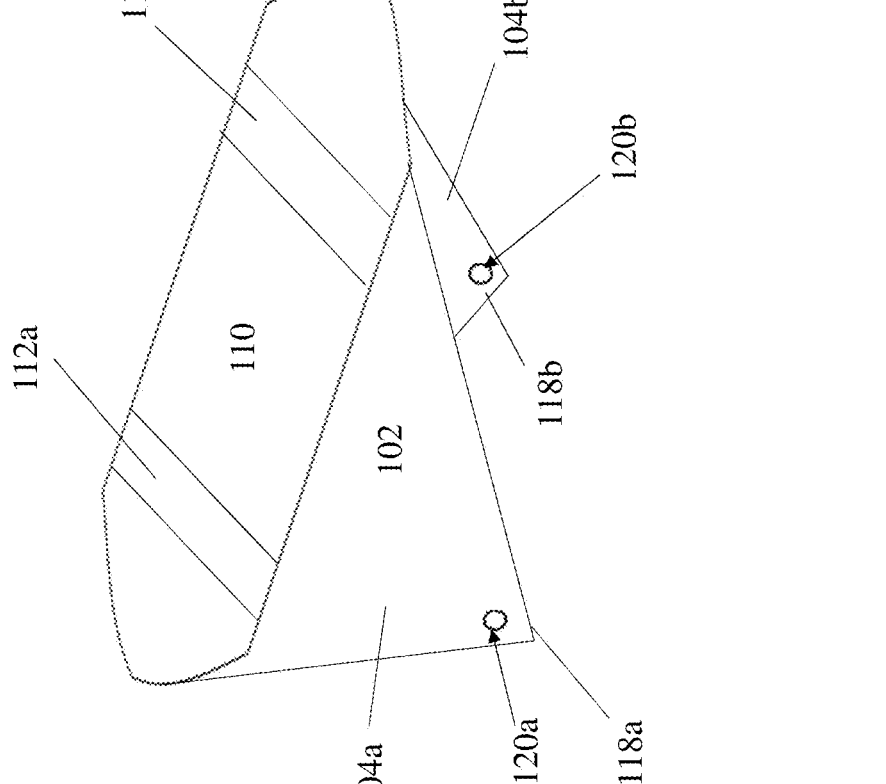
FIG. 4 shows a planar view of an exemplary wearable reusable shell, according to an embodiment of the present disclosure, wherein the pair of wings are in a folded configuration.

FIG. 4 shows a planar view of an exemplary wearable reusable shell 101, according to an embodiment of the present disclosure, wherein the pair of wings 104*a*, 104*b* are in a folded configuration. For instance, when the wearable reusable shell 101 is positioned on top of a groin portion of a user's undergarment, the pair of wings 104*a*, 104*b* may be folded along the side lengths of the center portion 106 of the base 102 from an unfolded configuration (see, e.g., FIGS. 1-2) into the folded configuration and wrapped around the groin portion of the undergarment to prevent bodily discharge from leaking onto, and subsequent soiling and staining, the user's clothing. In some embodiments, where an edge portion 118*a*, 118*b* of each of the pair of wings 104*a*, 104*b* comprises a mechanical fastener 120*a*, 120*b*, the wings 104*a*, 104*b* may be folded down into the folded configuration and the mechanical fasteners 120*a*, 120*b* coupled together, such that the wearable reusable shell 101 is secured to the user's undergarments. Accordingly, the wearable reusable shell 101 does not shift upon movement by the user (i.e., the wearable reusable shell 101 stays in place against the groin of a user over the course of everyday movement including walking, sitting, standing up, sleeping, etc.).

FIG. 5 shows a flowchart detailing an exemplary method 500 of making the wearable reusable shell 101 described herein, according to an embodiment of the present disclosure. In some embodiments, the method comprises a step 501 of providing a first base layer, a step 502 of placing an inner layer along a center portion of a top surface of the first base layer, a step 503 of placing an outer layer along the center portion of the first base layer and on top of the inner layer, a step 504 of placing at least one band across a width of the outer layer, and a step 505 of securing together the first base layer, the inner layer, the outer layer, and the at least one band along the center portion of the first base layer.

FIG. 6 shows a flowchart detailing an exemplary method 600 of using the wearable reusable shell 101 described herein, according to an embodiment of the present disclosure. In some embodiments, the method comprises a step 601 of securing the wearable reusable shell 101 to a user's undergarment and a step 602 of securing an absorbent article underneath at least one band on the wearable reusable shell.

According to the present disclosure, in some embodiments, a kit for a hybrid sanitary napkin comprises a wearable reusable shell 101 and an absorbent article configured to be positioned on top of the outer layer 110 and secured underneath the at least one band 112*a*, 112*b*. In some embodiments, the wearable reusable shell 101 may be provided as separate parts to be joined together (e.g., the base layers 102*a*, 102*b*, inner layer 108, outer layer 110, the at least one band 112*a*, 112*b*, mechanical fasteners 120*a*, 120*b*). The absorbent article may comprise a reusable or disposable material and may be insertable and removable from the wearable reusable shell 101. In some embodiments, the kit may further comprise an undergarment. In some embodiments, there is provided a hybrid sanitary napkin comprising a wearable reusable shell 101 and an absorbent article positioned on top of the outer layer 110 and secured underneath the at least one band 112*a*, 112*b*.

According to the present disclosure, in some embodiments, there is provided a method of making a wearable reusable shell 101 for an absorbent article comprising providing a first base layer 102*a*, wherein the first base layer 102*a* comprises a top surface, a bottom surface, and a pair of wings 104*a*, 104*b* extending from a center portion 106; placing an inner layer 108 along the center portion 106 of the top surface of the first base layer 102*a*, wherein the inner layer 108 comprises a biodegradable material; placing an outer layer 110 along the center portion 106 of the first base layer 102*a* and on top of the inner layer 108, wherein the outer layer 110 comprises a soft, absorbent material configured to be worn against the groin portion of a user; placing at least one band 112*a*, 112*b* across a width of the outer layer 110, wherein the at least one band 112*a*, 112*b* comprises an inner surface comprising a rubberized material; and securing together the first base layer 102*a*, the inner layer 108, the outer layer 110, and the at least one band 112*a*, 112*b* along the center portion 106 of the first base layer 102*a*. In some embodiments, the method further comprises securing a second base layer 102*b* to the bottom surface of the first base layer 102*a*. In some embodiments, the method further comprises securing a mechanical fastener 120*a*, 120*b* to an edge portion 118*a*, 118*b* of each of the pair of wings 104*a*, 104*b*. In some embodiments, the mechanical fastener 120*a*, 120*b* comprises at least one of a hook-and-loop fastener, male and female connector, zipper, lip and tape fastener, rivet and eyelet, cufflink, button, snap, clasp, eyelet and lace, and safety pin.

According to the present disclosure, in some embodiments, there is provided a method of using a wearable reusable shell 101 comprising securing the wearable reusable shell 101 to a user's undergarment and securing an absorbent article underneath the at least one band 112*a*, 112*b*. In some embodiments, the undergarment is underwear and securing the wearable reusable shell 101 to a user's undergarment comprises fastening together the mechanical fasteners 120*a*, 120*b* on each of the pair of wings 104*a*, 140*b* around a groin portion of the underwear. In some embodiments, the absorbent article comprises a disposable material.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A wearable reusable shell for a removable absorbent article for consisting of:
  a square or diamond-shaped base having four corners;
  an inner layer positioned diagonally along a center portion of the base to a first pair of opposite corners of the base;
  an outer layer positioned on top of the inner layer, wherein portions of the base not covered by the inner and outer layers form a pair of wings, each wing comprising a second pair of opposite corners of the base;
  at least one band extending over a center portion of a width of the outer layer, wherein the at least one band is configured to hold the removable absorbent article in place; and comprises a rubberized material on an inner surface of said at least one band; and
  a mechanical fastener positioned at the corner of each of the pair of wings, wherein the mechanical fastener is configured to secure the wearable reusable shell to an undergarment placed against a user's groin into which wearable reusable shell the removable absorbent article is secured.

2. The wearable reusable shell of claim 1, wherein the inner layer comprises a biodegradable material.

3. The wearable reusable shell of claim 1, wherein the outer layer comprises a soft, absorbent material, configured to be worn against the groin portion of a user.

4. The wearable reusable shell of claim 1, wherein the base comprises one or more fabric layers, wherein at least one of the one or more fabric layers comprises a printed pattern.

5. The wearable reusable shell of claim 1, wherein the rubberized material is a silicone strip.

6. The wearable reusable shell of claim 1, wherein the at least one band is elastic.

7. The wearable reusable shell of claim 1, wherein the mechanical fastener comprises at least one of a hook-and-loop fastener, male and female connector, zipper, lip and tape fastener, rivet and eyelet, cufflink, button, snap, clasp, eyelet and lace, and safety pin.

8. The wearable reusable shell of claim 1, wherein the mechanical fastener is a snap.

9. A method of making the wearable reusable shell of claim 1 comprising:
  providing a first square or diamond-shaped base layer comprising four corners, wherein the first base layer comprises a top surface and a bottom surface;
  placing an inner layer diagonally along a center portion of the top surface of the first base layer to two opposite corners of the base layer, wherein the inner layer comprises a biodegradable material;
  placing an outer layer on top of the inner layer, wherein the outer layer comprises a soft, absorbent material configured to be worn against the groin portion of a user, and wherein portions of the base not covered by the inner and outer layers form a pair of wings, each wing comprising one of a second pair of opposite corners of the base;
  placing at least one band across a center portion of a width of the outer layer, wherein the at least one band comprises an inner surface comprising a rubberized material; and
  securing together the first base layer, the inner layer, the outer layer, and the at least one band along the center portion of the first base layer.

10. The method of claim 9, further comprising securing a second base layer to the bottom surface of the first base layer.

11. The method of claim 9, further comprising securing a mechanical fastener to an edge portion of each of the pair of wings.

12. The method of claim 10, wherein the mechanical fastener comprises at least one of a hook-and-loop fastener, male and female connector, zipper, lip and tape fastener, rivet and eyelet, cufflink, button, snap, clasp, eyelet and lace, and safety pin.

* * * * *